(12) United States Patent
Nakaoka

(10) Patent No.: US 8,524,355 B2
(45) Date of Patent: *Sep. 3, 2013

(54) DISPOSABLE ABSORBENT ARTICLE

(75) Inventor: Kenji Nakaoka, Tsurugi-cho (JP)

(73) Assignee: Livedo Corporation, Ehime (JP)

( * ) Notice: Subject to any disclaimer, the term of this patent is extended or adjusted under 35 U.S.C. 154(b) by 765 days.

This patent is subject to a terminal disclaimer.

(21) Appl. No.: 10/555,869

(22) PCT Filed: May 10, 2004

(86) PCT No.: PCT/JP2004/006571
§ 371 (c)(1),
(2), (4) Date: Nov. 7, 2005

(87) PCT Pub. No.: WO2004/098473
PCT Pub. Date: Nov. 18, 2004

(65) Prior Publication Data
US 2007/0093164 A1   Apr. 26, 2007

(30) Foreign Application Priority Data

May 9, 2003   (JP) .................................. 2003-131741

(51) Int. Cl.
*B32B 27/12* (2006.01)

(52) U.S. Cl.
USPC ........... 428/198; 442/328; 442/329; 442/381; 442/385; 442/389; 442/393; 442/416; 442/417; 604/365; 604/366; 604/367; 604/368; 604/370; 604/375; 604/379; 604/380; 604/385.01; 604/385.24

(58) Field of Classification Search
USPC .................. 442/328, 381, 385, 352, 39, 394, 442/293, 327, 329, 353, 359, 366, 376, 382, 442/398, 399, 401, 409, 411, 389, 393, 416, 442/417; 602/41; 604/368, 378, 385.01, 604/367, 372, 380, 358, 365, 366, 370, 373, 604/379, 383, 384, 385.101, 385.23, 375, 604/385.24; 156/290, 73.1, 160, 161, 163, 156/164, 176, 209, 229, 252, 253, 308.4, 156/309.6, 553, 554, 555, 580.1, 580.2, 62.8; 264/156, 168, 210.2, 444, 546, 555, 571; 428/131, 136, 137, 138, 171, 103, 132, 195.1, 428/196, 198, 213, 220, 339, 913
See application file for complete search history.

(56) References Cited

U.S. PATENT DOCUMENTS 4,212,302 A  *  7/1980  Karami ......................... 604/368
RE32,957 E  *  6/1989  Elias et al. ..................... 604/368

(Continued)

FOREIGN PATENT DOCUMENTS

CN   1371671       10/2002
EP   1 609 448     12/2005

(Continued)

*Primary Examiner* — Elizabeth Cole
(74) *Attorney, Agent, or Firm* — Cermak Nakajima LLP; Tomoko Nakajima

(57) ABSTRACT

A disposable absorbent article includes an absorbent mat provided between a liquid-permeable top sheet and a liquid-impermeable back sheet. Herein, the absorbent mat includes a sheet-like water-absorbent layer that contains a water-absorbent resin powder but that does not contain pulp fibers, and a fiber assembly layer that contains both the water-absorbent resin powder and the pulp fibers, the sheet-like water-absorbent layer and the fiber assembly layer arranged sequentially in this order from a top sheet side. The fiber assembly layer includes a fiber presence region in which both the pulp fibers and the water-absorbent resin powder are present, and a fiber absence region in which both the pulp fibers and the water-absorbent resin powder are absent, the fiber presence region and the fiber absence region formed to be adjacent with each other.

5 Claims, 14 Drawing Sheets

(56) References Cited

U.S. PATENT DOCUMENTS

| | | | |
|---|---|---|---|
| 4,935,021 A | 6/1990 | Huffman et al. | |
| 5,411,497 A | 5/1995 | Tanzer et al. | |
| 5,489,469 A * | 2/1996 | Kobayashi et al. | 442/393 |
| 5,509,915 A * | 4/1996 | Hanson et al. | 604/378 |
| 5,601,542 A * | 2/1997 | Melius et al. | 604/368 |
| 5,895,379 A | 4/1999 | Litchholt et al. | |
| 6,080,909 A | 6/2000 | Osterdahl et al. | |
| 6,569,137 B2 * | 5/2003 | Suzuki et al. | 604/385.01 |
| 6,596,910 B2 | 7/2003 | Tung et al. | |
| 6,972,011 B2 * | 12/2005 | Maeda et al. | 604/385.01 |
| 2001/0014797 A1 * | 8/2001 | Suzuki et al. | 604/378 |
| 2002/0115969 A1 | 8/2002 | Maeda et al. | |
| 2006/0184146 A1 | 8/2006 | Suzuki | |

FOREIGN PATENT DOCUMENTS

| | | | |
|---|---|---|---|
| GB | 2 286 832 | | 8/1995 |
| JP | S54-1981698 | | 6/1978 |
| JP | H2-10824 | | 1/1990 |
| JP | 6-254118 | | 9/1994 |
| JP | 9-504210 | | 4/1997 |
| JP | 10168230 A | * | 6/1998 |
| JP | 2002-143215 | | 5/2002 |
| WO | WO-90/04374 | | 5/1990 |
| WO | WO-97/18783 | | 5/1997 |
| WO | WO-01/89439 | | 11/2001 |
| WO | WO 2004080361 A1 | * | 9/2004 |

* cited by examiner

25(35)

2c(3c)

25(35)

2c(3c)

DISPOSABLE ABSORBENT ARTICLE

BACKGROUND OF THE PRESENT INVENTION

1. Field of the Present Invention

The present invention relates to disposable absorbent articles such as disposable diapers and disposable pants.

2. Description of the Related Art

Recently, in the field of sanitary materials using disposable absorbent articles such as disposable diapers, disposable pants and sanitary napkins, demand for development of thin, comfortable absorbent articles for individuals who suffer from light to medium incontinence rises. As a disposable absorbent article for the light to medium incontinence, a pants-type absorbent article thinner and comfortable to wear without hampering a walking operation of a wearer is often desired.

A conventionally available absorbent article includes an absorbent between a liquid-permeable top sheet and a liquid-impermeable back sheet. As this absorbent, an absorbent mat obtained by forming fibrillated pulp fibers, absorbent resin powder, thermoplastic fiber or the like into a mat, and fixedly wrapping up the mat in thin paper or the like has been used.

In order to improve comfort to wear while maintaining an absorbing performance of the absorbent article that includes the absorbent mat, there is proposed a method for making the absorbent mat thinner by reducing the amount of the fibrillated pulp fibers that constitutes the absorbent mat and increasing the amount of the absorbent resin powder.

However, if the amount of the absorbent resin powder in the absorbent mat is increased so as to improve the absorbing performance, the swelling absorbent resin powder which has absorbed excretions such as urine often causes the absorbent mat to get out of shape.

As a very thin absorbent article that does not get out of shape after absorbing water, a water-absorbent multilayer member for a disposable product that does not contain pulp fiber other tha nonwoven fabrics and configured so that water-absorbent resin powder is held between two nonwoven fabrics by web-like hot melt adhesive has been proposed (W00189439).

According to this conventional technique, since the water-absorbent resin powder is fixedly retained by the web-like hot melt adhesive, the multilayer member does not get out of shape. In addition, the multilayer member does not contain the pulp fiber. Therefore, the very thin absorbent article comfortable for a wearer is provided. However, the component of the water-absorbent multilayer member that primarily exhibits the absorbing performance is the water-absorbent resin powder. Therefore, as compared with the conventional absorbent mat the absorbent of which mainly consists of the pulp fiber, the water-absorbent multilayer member is sometimes inferior in water absorption speed.

Further, even if many water-absorbent multilayer members are employed to secure a sufficient amount of water absorption, excrements cannot be smoothly introduced to the lower water-absorbent multilayer member. As a result, there is a probability that the water-absorbent resin cannot sufficiently exhibit its water absorption ability.

The present invention has been achieved in view of these circumstances. It is an object of the present invention to provide a disposable absorbent article including an absorbent mat that hardly gets out of shape even if absorbing a body fluid, that has a high water absorption speed, and that make a wearer who wears the article feel comfortable.

SUMMARY OF THE PRESENT INVENTION

A disposable absorbent article according to the present invention includes an absorbent mat provided between a liquid-permeable top sheet and a liquid-impermeable back sheet. Herein, the absorbent mat includes a sheet-like water-absorbent layer that contains a water-absorbent resin powder but that does not contain pulp fibers, and a fiber assembly layer that contains both the water-absorbent resin powder and the pulp fibers, the sheet-like water-absorbent layer and the fiber assembly layer arranged sequentially in this order from a top sheet side, and the fiber assembly layer includes a fiber presence region in which both the pulp fibers and the water-absorbent resin powder are present, and a fiber absence region in which both the pulp fibers and the water-absorbent resin powder are absent, the fiber presence region and the fiber absence region formed to be adjacent with each other.

By adopting this configuration, it is possible to speedily absorb the body fluid excreted from the wearer.

DETAILED DESCRIPTION OF THE PRESENT INVENTION

A disposable absorbent article according to the present invention includes an absorbent mat between a liquid-permeable top sheet and a liquid-impermeable back sheet. The present invention is most strongly characterized in that the absorbent mat includes a sheet-like water-absorbent layer that contains water-absorbent resin powder but does not contain pulp fiber, and a fiber assembly layer that contains both the pulp fiber and the water-absorbent resin powder in this order from a top sheet side and in that the fiber assembly layer is configured so that a fiber presence region that contains both the pulp fiber and the water-absorbent resin powder and a fiber absence region in which both the pulp fiber and the water-absorbent resin powder are absent are formed adjacently to each other.

By adopting the absorbent mat thus configured, it is possible to provide an absorbent article that less frequently gets out of shape even if absorbing the body fluid and that has a high absorption speed.

Figure 1:
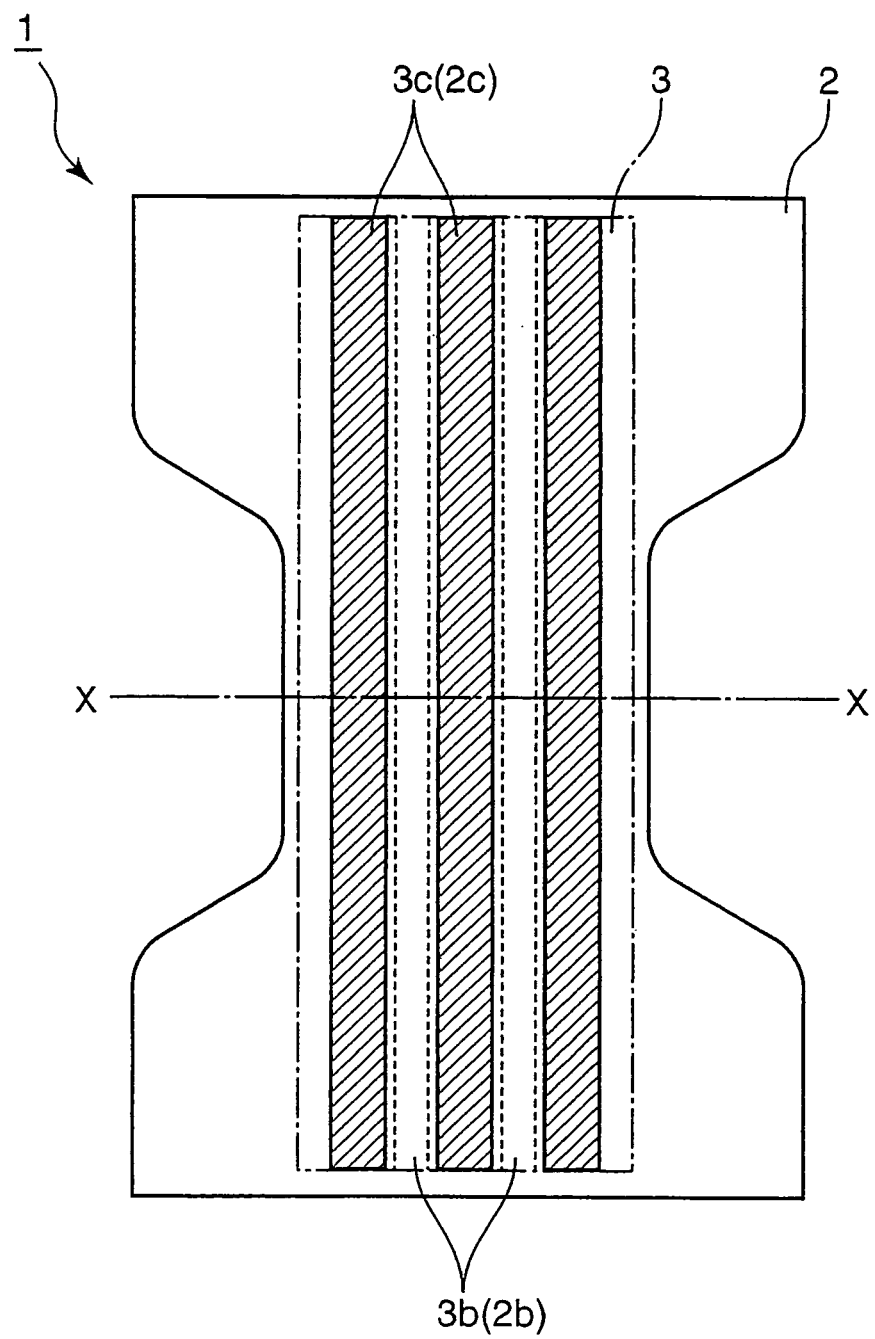
FIG. 1 is a plan view that illustrates an absorbent mat according to the present invention.
Figure 2:
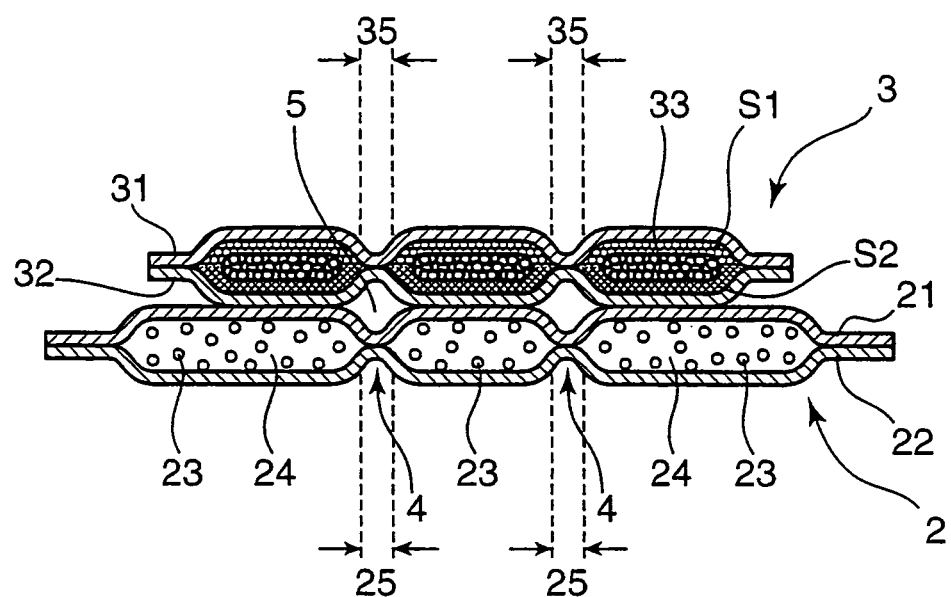
FIG. 2 is a schematic cross-sectional view of the absorbent mat.

FIG. 1 is a plan view that illustrates a typical embodiment of an absorbent mat used in the absorbent article according to the present invention, and FIG. 2 is a schematic cross-sectional view taken along a line X-X of FIG. 1. Referring to FIG. 1 and FIG. 2, reference symbol 1 denotes the absorbent mat, reference symbol 2 denotes a fiber assembly layer, and reference symbol 3 denotes a sheet-like water-absorbent layer.

The fiber assembly layer that constitutes the absorbent mat will first be described.

The fiber assembly layer 2 is placed below the sheet-like water-absorbent layer 3 in the absorbent mat 1 according to the present invention. The fiber assembly layer 2 is essential to secure that an absorbent article including the absorbent mat 1 exhibit a sufficient of water absorption and to realize absorption at high speed.

Figure 3:
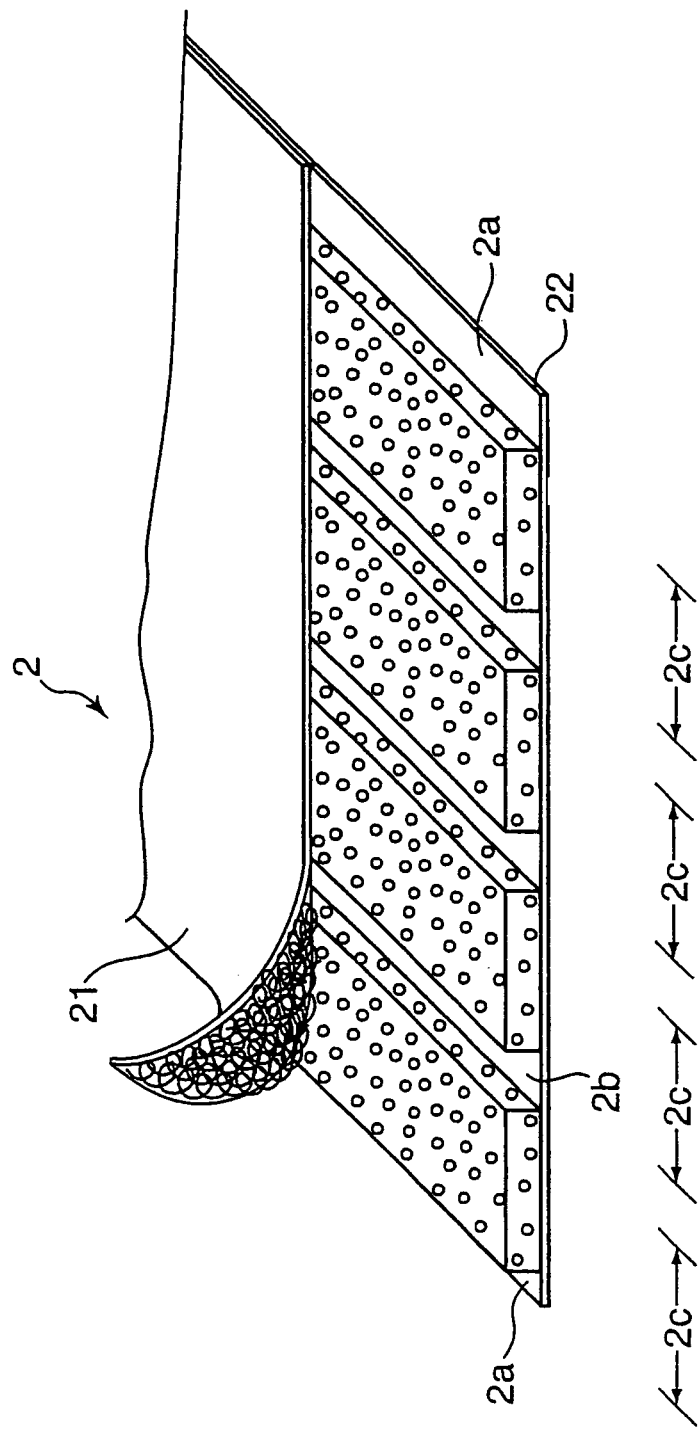
FIG. 3 is a partially cut-out perspective view of a fiber assembly layer according to the present invention.
Figure 4:
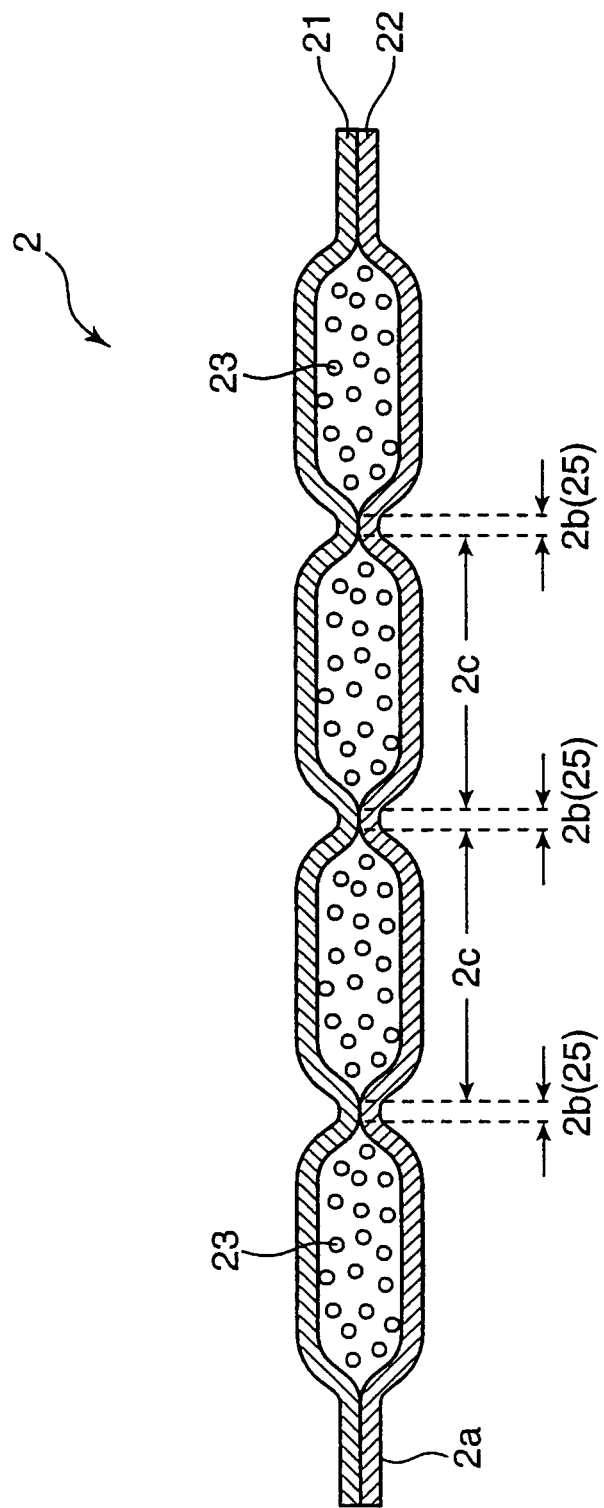
FIG. 4 is a schematic cross-sectional view of the fiber assembly layer.

FIG. 3 and FIG. 4 are a partially cut-out perspective view and a schematic cross-sectional view of the fiber assembly layer, respectively. The fiber assembly layer 2 is formed by wrapping up both pulp fiber 24 and water-absorbent resin powder 23 between an upper covering sheet 21 and a lower covering sheet 22. According to the present invention, to provide a thin absorbent article exhibiting a good water absorbing performance without making a wearer feel uncomfortable, a fixed amount of water-absorbent resin powder is contained in the fiber assembly layer 2 as well as the sheet-like water-absorbent layer 3 to be describe later.

Herein, reference symbol 2a denotes a fiber absence region ("end region 2a") formed on each end of the fiber assembly layer 2 in a width direction. Reference symbol 2b denotes a fiber absence region (hereinafter, "intermediate region 2b") in which both the pulp fiber and the water-absorbent resin powder are substantially absent. Reference symbol 2c denotes a fiber presence region in which both the pulp fiber and the water-absorbent resin powder are present. Namely, the fiber presence regions 2c are present in the fiber assembly layer 2 to be continuous in a longitudinal direction of the upper (lower) covering sheet and to be separated from adjacent regions 2c by the fiber absence regions in the width direction.

The upper covering sheet 21 and the lower covering sheet 22 are bonded to each other in the fiber absence regions 2a and 2b. Accordingly, the water absorbent layer 3 and the fiber assembly layer 2 are detached at a location of the water-absorbent resin powder absence region 3b and the fiber absence region 2b. The water absorbtion resin powder absence regions 3b is formed between the water-absorbent resin powder presence regions 3c. The fiber absence region 2b is formed between the fiber presence regions 2c. Both the pulp fibers 24 and the water-absorbent resin powder 23 are absent in the fiber absence region 2b. The fiber absence region 2b (gap portion 25) may be formed by sealing the upper and lower covering sheets 21 and 22 located in the fiber absence regions 2b to each other by means such as a hot melt adhesive, a heat seal or an ultrasonic seal.

While a thickness of this fiber assembly layer 2 is not limited to a specific value, it is preferably 1 to 8 mm.

Figure 5:
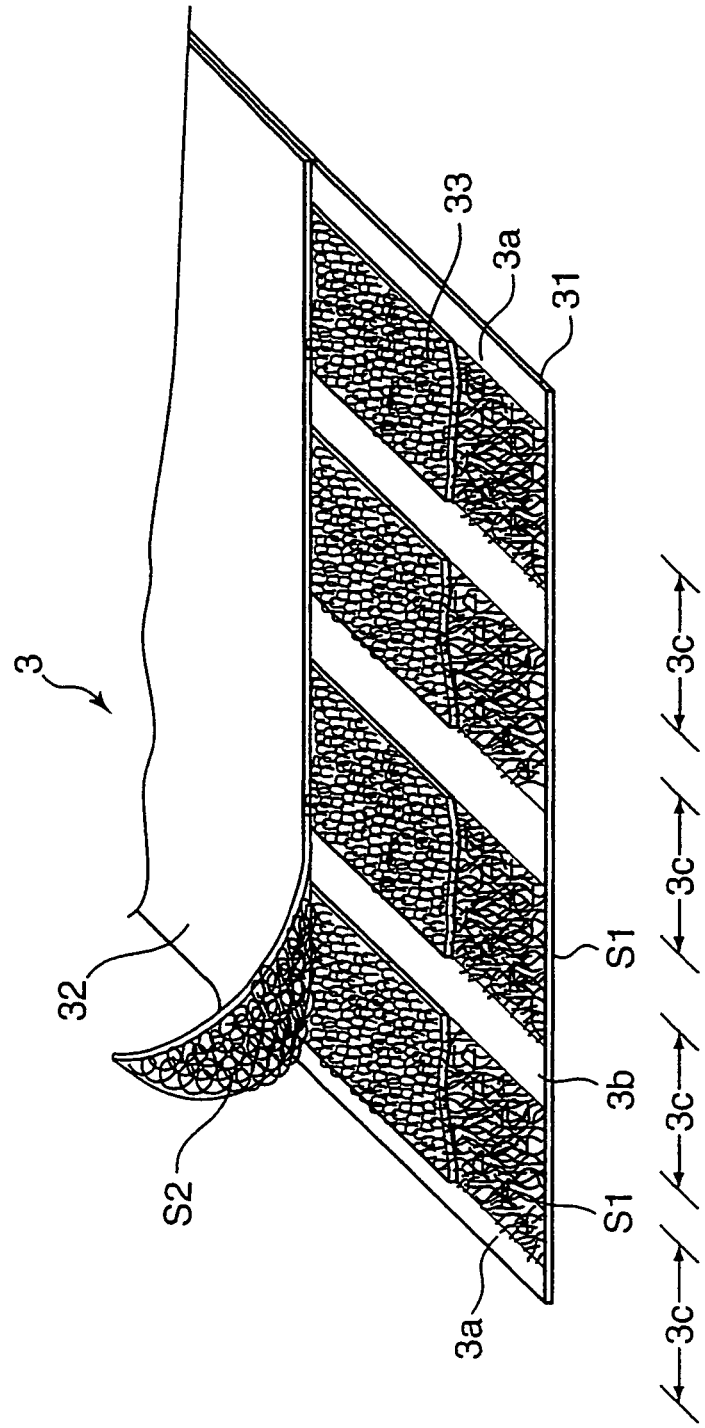
FIG. 5 is a partially cut-out perspective view of a sheet-like water-absorbent layer according to the present invention.
Figure 6:
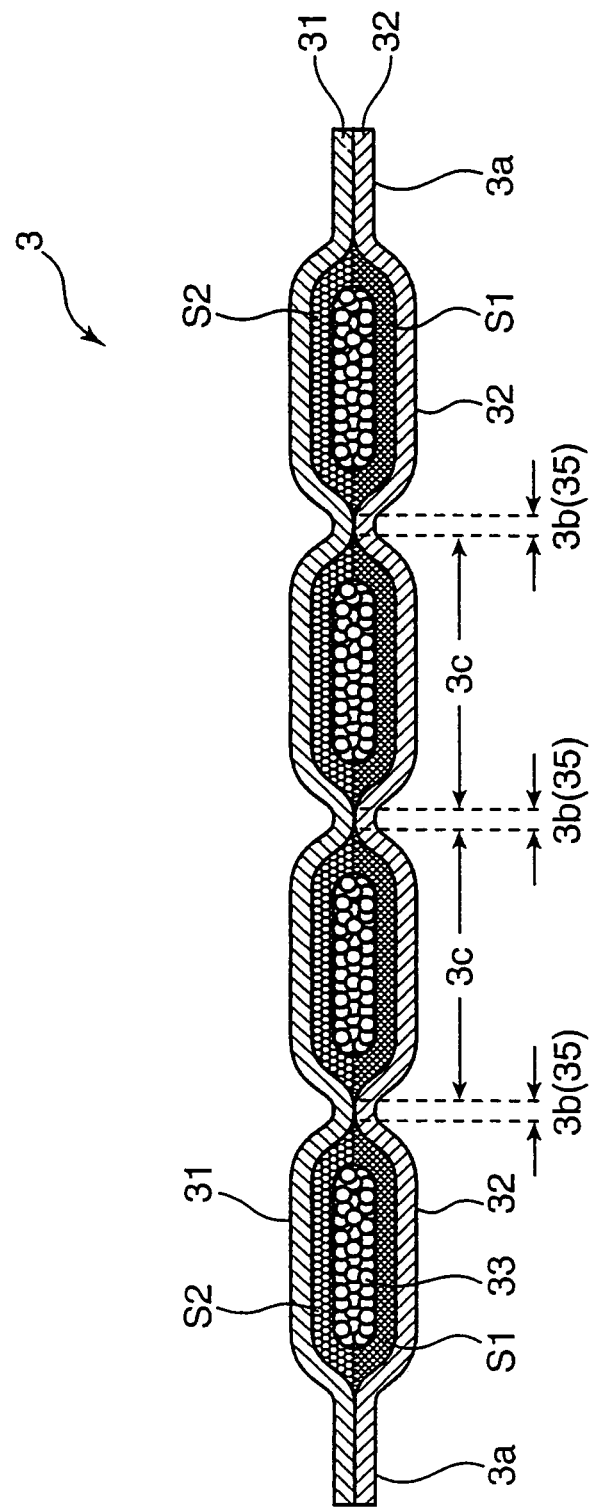
FIG. 6 is a schematic cross-sectional view of the sheet-like water-absorbent layer.

The sheet-like water-absorbent layer 3 will next be described. FIG. 5 and FIG. 6 are a partially cut-out perspective view and a schematic cross-sectional view of the sheet-like water-absorbent layer according to a typical embodiment of the present invention, respectively. The sheet-like water-absorbent layer 3 is configured so that water-absorbent resin powder 33 is held between a first nonwoven fabric sheet 31 and a second nonwoven fabric sheet 32 substantially equal in area and shape to the first nonwoven fabric 31. This water-absorbent resin powder 33 is fixedly bonded to the respective nonwoven fabric sheets by a first adhesive layer S1 applied onto the first nonwoven fabric sheet 31 and a second adhesive layer S2 applied onto the second nonwoven fabric sheet 32, respectively.

Herein, reference symbol 3a denotes a water-absorbent resin powder absence region (hereinafter, "end region 3a") on each end of the sheet-like water-absorbent layer in a width direction. Reference symbol 3b denotes a water-absorbent resin powder absence region (hereinafter, "intermediate region 3b") provided in an intermediate portion of the sheet-like water-absorbent layer. Reference symbol 3c denotes a water-absorbent resin powder presence region. Namely, in FIG. 5, a plurality of water-absorbent resin powder presence regions 3c are present to be continuous in a longitudinal direction of the nonwoven fabric sheets 31 and 32 and to be separated from adjacent regions 3c by the water-absorbent resin powder absence region 3b in a width direction thereof.

The first and second nonwoven fabric sheets 31 and 32 are bonded to each other in the end regions 3a and the intermediate region 3b in which the water-absorbent resin powder is absent. Namely, the water-absorbent resin powder presence regions 3c are partitioned from the adjacent water-absorbent resin powder presence regions 3c by sealing portion 35. In FIG. 5 and FIG. 6, an example of arranging the adhesive layers S1 and S2 only in the water-absorbent resin presence regions 3c is shown. Alternatively, the adhesive layers S1 and S2 may be arranged not only in the water-absorbent resin powder presence regions 3c but also in the water-absorbent resin powder absence regions. In addition, the sealing portions 35 may be formed by sealing the regions 3c by means such as a heat seal or ultrasonic bonding.

The sheet-like water-absorbent layer 3 is placed on the fiber assembly layer 2, and the sheet-like water-absorbent layer 3 located on a skin side of the wearer who wears the absorbent article, thereby obtaining the absorbent mat 1.

As illustrated in FIG. 2, the absorbent mat 1 is preferably configured so that the sheet-like water-absorbent layer 3 is placed on the fiber assembly layer 2 so as to cause all of or a part of the sealing portions 35 corresponding to the intermediate regions 3b of the water-absorbent layer 3 to be located above the gap portions 25 (fiber absence regions 2b) of the fiber assembly layer 2. With this configuration, the water absorption speed is accelerated.

Namely, the body fluid discharged from the wearer is absorbed by the water-absorbent resin powder 33 of the sheet-like water-absorbent layer 3 and, at the same time, the body fluid is moved to the lower-side fiber assembly layer 2 through the sealing portions 35. The body fluid that reaches the fiber assembly layer 2 is partly absorbed by the upper fiber assembly 21 and partly reaches the lowermost liquid-impermeable back sheet through the openings 25 of the upper fiber assembly layer 21. The body fluid that reaches the back sheet is absorbed by the fiber assembly layer 2 while being diffused in the length direction of the absorbent mat 1 through cavities 4 between the gap portions 25 of the fiber assembly layer 2 and the liquid-impermeable back sheet 12 (see FIG. 15). By thus providing a multilayer state in which the gap portions 25 vertically face the sealing portions 35, the discharged body fluid is promptly moved to the lower side of the absorbent mat 1 and diffused into the absorbent mat without waiting for the body fluid to be absorbed by the sheet-like water-absorbent layer 3 and the fiber assembly layer 2. This enables the fiber assembly layer 2 under the sheet-like water-absorbent layer 3 to absorb the body fluid substantially simultaneously with the discharge of the body fluid. As a result, the absorption speed is accelerated.

Figure 7A:
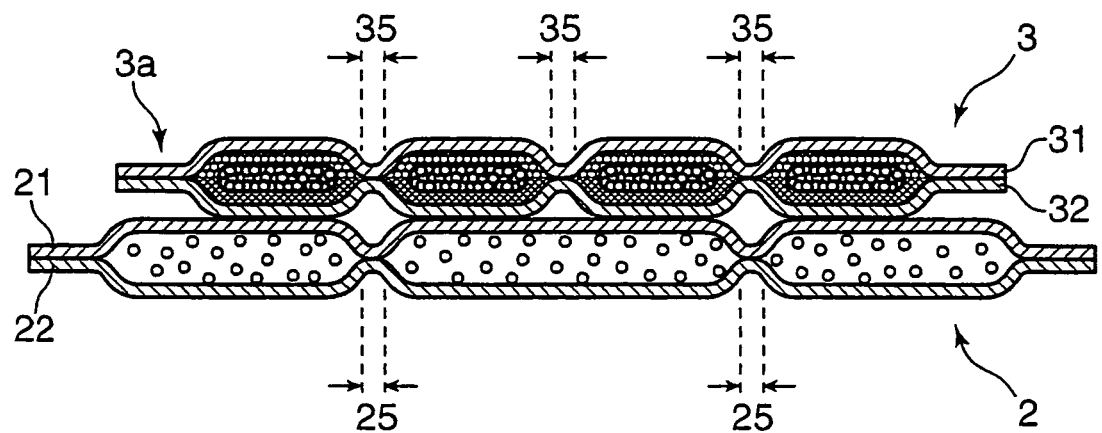
FIG. 7A and FIG. 7B are schematic cross-sectional views that illustrate a multilayer state of the fiber assembly layer and the sheet-like absorbent layer according to the present invention.
Figure 7B:
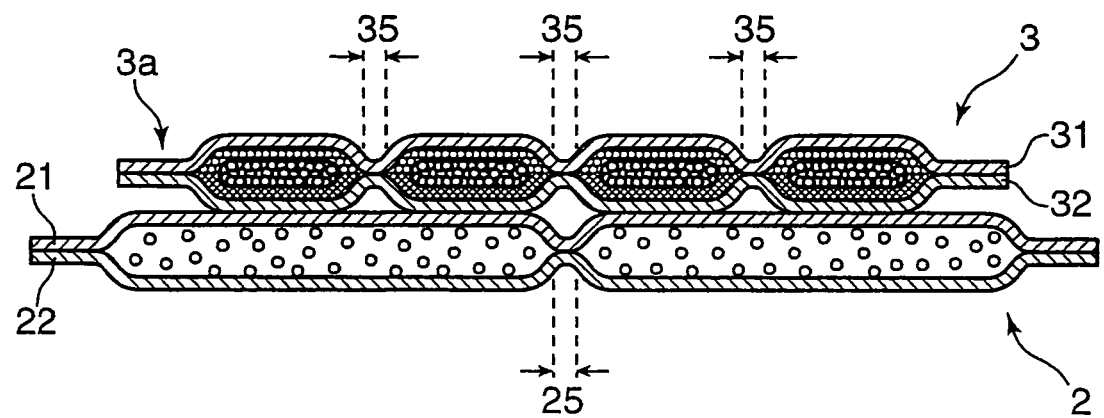

Needless to say, it is preferable that the gap portions 25 of the fiber assembly layer 2 completely coincide with the sealing portions 35 of the sheet-like water-absorbent layer 3 as illustrated in FIG. 2 because the body fluid is absorbed at higher speed. However, it is sufficient that the gap portions 25 partially coincide with the sealing portions 35 in the vertical direction as illustrated in, for example, FIG. 7A and FIG. 7B. In FIG. 7A, the body fluid that has passed through the sealing portions 35 of the sheet-like water-absorbent layer 3 is promptly moved to the lowermost layer through the gap portions 25 of the fiber assembly layer 2 located under the sheet-like water-absorbent layer 3. The body fluid that has passed through the sealing portion 35 provided in a central portion of the sheet-like water-absorbent layer 3 is absorbed by the fiber assembly layer 2 located under the sheet-like water-absorbent layer 3 and diffused by the gap portion 25. In order to make the absorption speed higher, it is preferable that the gap portion 25 and the sealing portion 35 are located in a portion corresponding to a portion right under an excretory part of the wearer as illustrated in FIG. 7B.

It is noted that the fiber presence regions 2c are preferably present under the both end regions 3a of the sheet-like water-absorbent layer 3, respectively. This is because the body fluid flowing to ends of the absorbent article is absorbed and lateral leakage of the body fluid can be prevented when, for example, the wearer turns sideways.

Further, the fact that the water-absorbent resin powder 33 contained in the sheet-like water-absorbent layer 3 that constitutes the absorbent mat 1 according to the present invention absorbs the body fluid and swells allows the absorbent mat 1 to exhibit the following features (1) to (3).

(1) The sheet-like water-absorbent layer 3 expands by water absorption and swelling of the water-absorbent resin powder 33, whereby the wet back of the body fluid that has been absorbed can be prevented.

Figure 8:
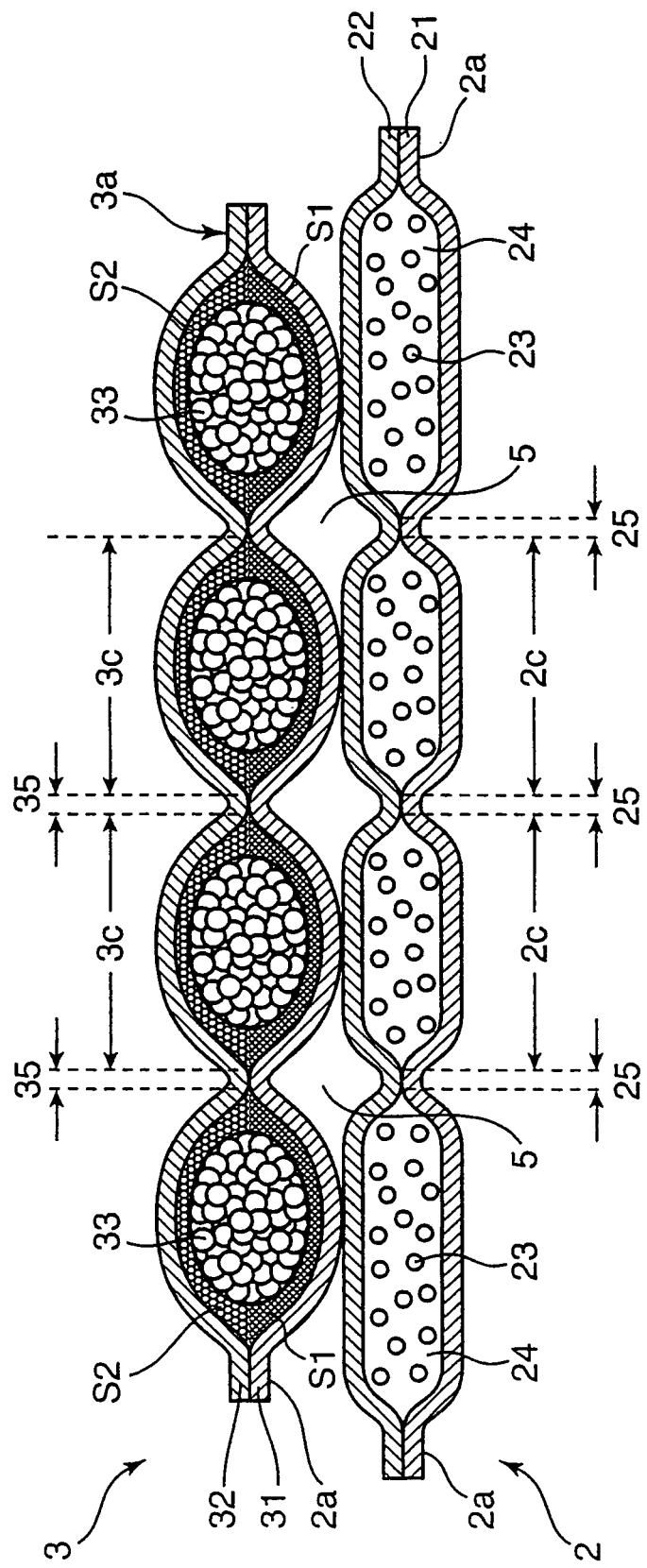
FIG. 8 is a schematic cross-sectional view that illustrates a swelling stat of the absorbent mat.

FIG. 8 illustrates a state in which the absorbent mat 1 according to the present invention has absorbed the body fluid. Herein, reference symbol 2 denotes the aforementioned fiber assembly layer and reference symbol 3 denotes the sheet-like water-absorbent layer. As illustrated in FIG. 8, the water-absorbent resin powder 33 contained in the sheet-like water-absorbent layer 3 absorbs the body fluid discharged from the wearer and swells. At this time, a volume of the water-absorbent resin powder 33 is increased in an expansion range allowed by the nonwoven fabric sheets 31 and 32 in the water-absorbent resin powder presence regions 3c partitioned by the sealing portions 35, 35 thereby increasing a thickness of the sheet-like water-absorbent layer 3. As a result, a distance between the fiber assembly layer 2 provided below the sheet-like water-absorbent layer 3 and the skin of the wearer is largely widened.

In the fiber assembly layer 2, many spaces are present among fibers, and the water-absorbent resin powder 23 contained in the fiber assembly layer 2 is present to be distributed without concentrating on one portion. During water absorption, therefore, the spaces act as those in which the fiber or water-absorbent resin powder 23 swell, so that a thickness of the fiber assembly layer 2 is not extremely changed before and after the absorption of the body fluid.

In general, the phenomenon of the backflow (wet back) of the body fluid in the absorbent article derives from the presence of the fiber assembly layer included in the article. The fiber assembly layer holds the excreted body fluid mainly in the spaces among the fibers. Accordingly, the body fluid held among the fibers easily oozes out to surfaces of the fiber assembly layer if the fiber assembly layer is pressurized somehow or other. The water-absorbent resin, by contrast, strongly holds the absorbed body fluid inside. Even if the resin is pressurized, the body fluid absorbed once by the water-absorbent resin powder hardly oozes out again to surfaces of the resin.

In the absorbent article according to the present invention, if the sheet-like water-absorbent layer 3 absorbs the body fluid once, the thickness of the layer 3 is increased by swelling of the water-absorbent resin 33. The distance between the fiber assembly layer 2 serving as the final water holding layer and the skin of the wearer is widened. Thus, even if the fiber assembly layer 2 is pressurized and the body fluid oozes out from the fiber assembly layer 2, it is difficult for this body fluid to overpass the sheet-like water-absorbent layer 3 thus thickened and to reach a top sheet 9 (see FIG. 15), thereby effectively suppressing the backflow of the body fluid.

(2) The cavities generated between the fiber assembly layer and the sheet-like water-absorbent layer enables the body fluid to be diffused and absorbed.

As already described, the absorption speed is accelerated by locating the gap portions 25 of the fiber assembly layer 2 and the sealing portions 35 of the sheet-like water-absorbent layer 3 to face each other. In addition, if the water-absorbent resin powder absence regions 3a and 3b of the sheet-like water-absorbent layer 3 are present above the fiber presence regions 2c of the fiber assembly layer 2, the sealing portions 35 provided in the water-absorbent resin powder absence regions 3a and 3b gradually rise from their positions before water absorption upward in the thickness direction, following the swelling of the water-absorbent resin powder 33. As a result, cavity 5 is generated between the fiber assembly layer 2 and the sealing portion 35 (see FIG. 8). The body fluid passed through the sealing portion 35 or the body fluid oozing out from the pressurized fiber assembly layer 2 is diffused in the length direction of the absorbent article through the cavity 5. Therefore, the presence of the cavity 5 also contributes to preventing the backflow of the body fluid.

The cavity 5 generated between the fiber assembly layer 2 and the sheet-like water-absorbent layer 3 effectively functions when the article absorbs the body fluid excreted at the second time and the following. Namely, the amount of water absorbable by the sheet-like water-absorbent layer 3 is limited. Due to this, if the body fluid is already absorbed up to the limit amount, a new body fluid cannot be absorbed even when the body fluid is excreted. However, if the cavity 5 is present below the sheet-like water-absorbent layer 3, the body fluid that cannot be absorbed can be diffused into portions that have enough room to absorb the fluid in the fiber assembly layer 2 through the gaps and absorbed.

(3) Further, since the sheet-like water-absorbent layer 3 prevents the body fluid from passing from the fiber assembly layer 2 to an upside of the sheet-like water-absorbent layer 3, the sheet-like water-absorbent layer 3 contribute to preventing the backflow of the body fluid. Namely, when the body fluid is absorbed, the water-absorbent resin powder regions 3c of the sheet-like water-absorbent layer 3 are in a state in which the swelling water-absorbent resin powder 33 is densely packed, so that it is difficult for the fluid to pass through the regions 3c.

It is noted, however, that the swelling water-absorbent resin powder presence regions 3c not only prevents the backflow of the body fluid from the fiber assembly layer but also sometimes prevent the newly excreted body fluid from passing through the sheet-like water-absorbent layer. Nevertheless, the sheet-like water-absorbent layer 3 according to the present invention includes the sealing portions 35 (intermediate region 3b) and the water-absorbent resin is not present in these sealing portions 35 or even if present, the amount of the powder is quite small. The newly excreted body fluid can, therefore, promptly move to the fiber assembly layer 2 through the sealing portions 35. It is possible to ensure absorbing the body fluid excreted at the second time and subsequent times.

According to the present invention, the sheet-like water-absorbent layer 3 and the fiber assembly layer 2 are configured as described above, whereby it is possible to ensure the sufficient amount of water absorption that enables promptly absorbing even the body fluid excreted at the second time and subsequent times. Besides, it is possible to suppress the backflow of the body fluid to a low level, prevent the skin of the wearer from being contaminated, and keep the skin clean.

The sheet-like water-absorbent layer 3 is a layer consisting of the absorbent resin powder and having a relatively high rigidity. Accordingly, even if the absorbent mat 1 is rubbed by a motion of the wearer, the rigidity of the sheet-like water-absorbent layer 3 prevent the fiber assembly layer 2 from being twisted or deformed, thus contributing to holding the entire shape of the absorbent mat 1.

The fiber assembly layer 2 according to the present invention contains not only fibrillated pulp fibers for securing water absorbing ability and thermofusible fiber for improving shape holding ability, but also water-absorbent resin powder dispersed into the fibrillated pulp fibers and the thermofusible fiber. As this fibrillated pulp fibers, well-known pulp fiber may be used. As the thermofusible fiber, polyolefin-based fiber such as polyethylene fiber or polypropylene fiber, polyester-based fiber, composite fiber or the like may be used. In addition, to improve the shape holding ability, hydrophilic fiber such as rayon fiber or cotton fiber may be added to the fiber assembly layer 2.

As the water-absorbent resin powder dispersed into the fiber assembly layer 2, well-known water-absorbent resin may be used. Examples of the well-known water-absorbent resin include the polyacrylic acid type, the cellulose type, starch-acrylonitrile type, and the like. An amount of the water-absorbent resin powder is used therein may preferably be in the range of 70% by mass or more to 120% by mass or less, relative to the amount of the fibrillated pulp fibers used in the fiber assembly layer. If the amount of the water-absorbent resin exceeds 120% by mass, the amount of resin is so excessive that the fiber assembly layer gives a stiff impression as a whole. In addition, the swelling water-absorbent resin may cause the absorbent mat to get out of shape. If the amount of the water-absorbent resin is smaller than 70% by mass, the amount of the water-absorbent resin powder is so small that it would be difficult to obtain a sufficient amount of absorption as that of the thin absorbent article.

The fibers and the water-absorbent resin powder are mixed up and integrated with one another to form an integral fiber assembly layer. Alternatively, the fibers are formed into a compact, the water-absorbent resin powder is dispersed into the compact, thereby forming a fiber assembly layer. It is preferable to apply a mechanical pressure to the integral fiber assembly layer while heating the layer so as to stabilize the shape of the layer. Thereafter, portions of the fiber assembly layer corresponding to the fiber absence regions are hollowed out and wrapped up in a covering sheet. Alternatively, fiber portions that constitute the fiber presence regions are produced in advance and arranged on a covering sheet so that the fiber presence regions and the fiber absence regions are present, and wrapped up in the covering sheet. The fiber assembly layer 2 may be held between upper and lower covering sheets as illustrated in FIG. 3, or may be wrapped up in one covering sheet. At this time, the fiber assembly layer may be fixed to the covering sheet or sheets using a hot melt adhesive or the like.

Figure 9A:
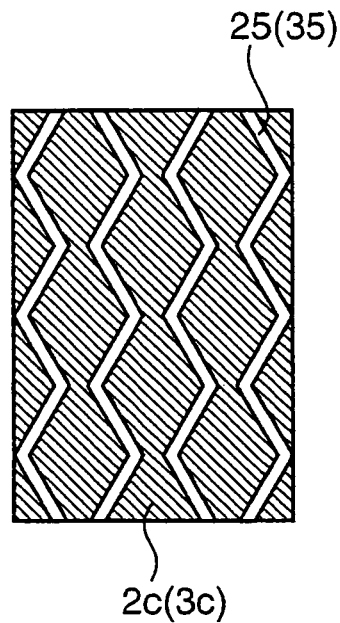
FIG. 9A and FIG. 9B are plan views that illustrate a gap portion provided in the fiber assembly layer and a sealing portion provided on the sheet-like water-absorbent layer according to the present invention.

The fiber absence region 2b may be formed zigzag as illustrated in FIG. 9A instead of being formed to extend linearly along the longitudinal direction of the absorbent article according to the present invention. If the fiber absence region 2b (or gap portion 25) is zigzag-formed, a contact area between the gap portion 25 and the fiber presence region 2c is made large as compared with the fiber absence region 2b formed linearly. Therefore, the diffusion of the body fluid is further promoted.

Figure 10:
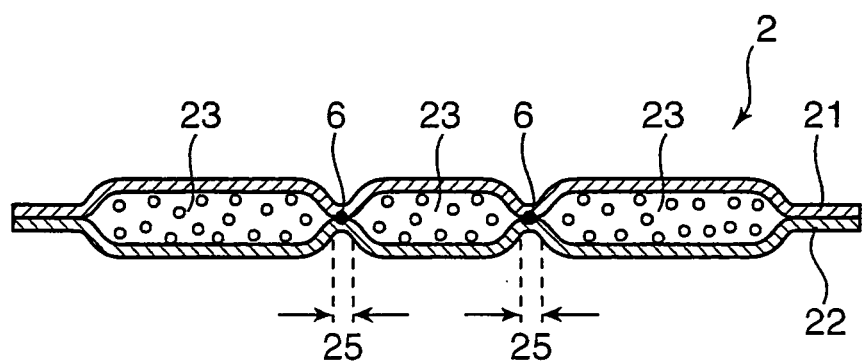
FIG. 10 is a schematic cross-sectional view of another fiber assembly layer according to the present invention.

The fiber assembly layer 2 tends to be bent in the width direction of the fiber assembly layer 2 because of the presence of the fiber absence regions 2b. Accordingly, the fiber assembly layer 2 tends to follow a body shape of the wearer. To further improve the wear's sense of fit to the absorbent article, elastic member 6 may be bonded and fixed to the respective fiber absence regions 2b in expanded states along the longitudinal direction of the regions 2b (FIG. 10). A stretching action of the elastic members 6 causes the upper and lower covering sheets in the gap portions 25 to contract, thereby making it easier for the fiber assembly layer 2 to follow a motion of the wearer and improving the wearer's sense of fit to the absorbent article. Further, by contracting the elastic member 6, a force for lifting up the absorbent mat acts on the absorbent article, which can prevent gaps from being generated between the wearer and the absorbent article and thus prevent lateral leakage of the body fluid.

The elastic member 6 may be fixedly held between the upper and lower covering sheets 21 and 22 in the respective fiber absence regions 2b of the fiber assembly layer 2. A fixing method is not limited to a specific one. Examples of the fixing method include thermal fusion bonding, ultrasonic fusion bonding, and fixing using the hot melt adhesive. Among them, it is preferable to adopt the fixing method using the hot melt adhesive. Each elastic member 6 may be an appropriate elastic member normally employed in disposable diapers. Examples of the elastic member include polyurethane and natural rubber. They can be used in a filamentous or film form.

The elastic member 6 is provided not only in the fiber absence regions of the fiber assembly layer but also between the covering sheets that constitute the absorbent article to be described later (see FIG. 15B to FIG. 15D).

An appropriate material is used for the covering sheets 21 and 22 such as tissue paper or a plastic film as long as it can permeate the body fluid. Specifically, examples of the liquid-permeable sheet material include liquid-permeable sheet materials normally used for disposable absorbent articles such as a nonwoven fabric using hydrophilic fibers such as cellulose, rayon or cotton fibers, a nonwoven fabric using hydrophobic fibers such as polypropylene, polyethylene, polyester or polyamide fibers, a surface of each of which is treated by a surfactant to provide a permeable material, and a plastic film including openings. Among them, the nonwoven fabric mainly consisting of polypropylene is preferably used. More preferably, the nonwoven fabric formed out of fine fibers having 1.0 to 3.0 decitexes by spunbonding and excellent in water permeability is used.

Figure 9B:
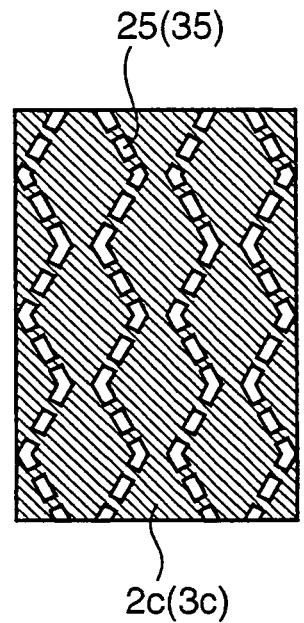

After the fiber assembly layer 2 is wrapped up in the covering sheets, the gap portions 25 are formed by bonding the covering sheets to each other in the fiber absence regions 2b or by bonding them using heat seals, ultrasonic seals or the like. The gap portions 25 should be provided so that at least adjacent fiber presence regions 2c are present independent of one another. With this configuration, the shape of the fiber assembly layer 2 can be held even if the fiber assembly layer 2 absorbs the body fluid Each gap portion 25 needs to have a sufficient strength to prevent breakdown by absorption of the body fluid. Examples of means for forming such gap portions 25 include bonding by the heat seal or hot melt adhesive, ultrasonic bonding, and stitching. The gap portions may be continuously bonded along the fiber absence regions. Alternatively, as illustrated in FIG. 9B, the gap portions may be intermittently bonded.

An entire plane shape of the fiber assembly layer 2 may be appropriately determined according to purposes and may be, for example, gourd-shaped, rectangular or hour glass-shaped.

For the first nonwoven sheet 31 and the second nonwoven sheet 32 of the sheet-like water-absorbent layer 3 according to the present invention, a liquid-permeable nonwoven fabric may be used. The same liquid-permeable nonwoven fabric as that for the fiber assembly layer may be used for the sheets 31 and 32. In addition, if the sealing portions 35 are to be formed by heat seals, a nonwoven fabric exhibiting a heat sealing property may be used. The nonwoven fabric sheets 31 and 32 may be formed by multilayer nonwoven fabrics.

The adhesive layers S1 and S2 provided in the nonwoven fabric sheets 31 and 32, respectively are layers for adhering the water-absorbent resin powder 33 to the respective sheets 31 and 32. The adhesive layers S1 and S2 are, therefore, preferably formed to be netted so as to be able to secure air-permeability without hampering the water absorption and the swelling while preventing falling of the water-absorbent resin powder 33.

To form the adhesive layers S1 and S2 to be netted, a method (a curtain spray method or a spiral coating method) for discharging molten adhesives in a filamentous form from a plurality of nozzles is simple and preferably used. Specifically, using a curtain spray coater configured so that a plurality of small discharge holes are arranged linearly and so that an air injection port capable of injecting hot air at high speed is provided in the vicinity of each discharge hole, the air is blown off to the molten adhesive discharged from each discharge hole. As a result, the adhesive can be applied as a netted assembly in which many filamentous adhesives randomly adhere to one another. In addition, using a spiral spray nozzle gun configured so that three or more air injection ports capable of blowing off the air in a direction of a center of the nozzle are provided point symmetrically in the vicinity of the hot melt adhesive discharge port, spiral adhesive layers can be formed on the respective nonwoven fabric sheets. In FIG. 5, an example of applying the adhesive layer S1 by the curtain spray method and the adhesive layer S2 by the spiral coating method is shown. However, the methods for forming the adhesive layers S1 and S2 are not limited to those illustrated in FIG. 5 and the adhesive layers S1 and S2 can be arbitrarily formed.

Each of the adhesive layers S1 and S2 may include a plurality of adhesive application portions or may be applied to an entire surface of each nonwoven fabric sheet.

As adhesives used for the first adhesive layer S1 and the second adhesive layer S2, the same type or different types of adhesives can be used and the types are not limited to specific ones. For examples, hot melt adhesives containing rubber such as natural rubber type, butyl rubber type or polyisoprene rubber type, styrene-type elastomer such as SIS, SBS, SIBS, SEBS or SEPS, ethylene-vinyl acetate copolymer (EVA), polyester, acrylic type, or polyolefin-type elastomer are used. Each adhesive preferably has an adhesive force capable of preventing the falling of the water-absorbent resin after the water absorption and has an expansion to be able to follow the swelling of the water-absorbent resin. In these respects, rubber or styrene-type elastomer adhesive is preferably used.

As the water-absorbent resin used in the sheet-like water-absorbent layer 3, the same resin as that used in the aforementioned fiber assembly layer is used.

In the sheet-like water-absorbent layer 3, the water-absorbent resin powder presence regions 3c are vertically held between the nonwoven fabric sheets 31 and 32, and the nonwoven fabric sheets 31 and 32 are sealed in the water-absorbent resin powder absence regions. Due to this, there is a limit to the space in which the water-absorbent resin powder 33 can swell. To appropriately carry out the present invention, therefore, the dispersion amount of the water-absorbent resin powder 33 may preferably be in the range of 100 g/m$^2$ or greater to 250 g/m$^2$ or smaller, relative to each presence region. If the amount is less than 100 g/m$^2$, it is difficult to secure the sufficient water absorbing capacity and maintain the sufficient distance between the fiber assembly layer 2 and the skin of the wearer after the swelling. If the amount exceeds 250 g/m$^2$, cost is increased. The dispersion amount of the water-absorbent resin powder 33 may preferably be in the range of 130 g/m$^2$ or greater to 220 g/m$^2$ or smaller, more preferably be in the range of 150 g/m$^2$ or greater to 200 g/m$^2$ or smaller.

After thus forming the adhesive layers S1 and S2 on the respective nonwoven fabric sheets 31 and 32 and attaching the water-absorbent resin powder 33 to the layers S1 and S2, the nonwoven fabric sheets 31 and 32 are bonded together and all of or part of the water-absorbent resin powder presence regions 3a and 3b are sealed. The sealing portions 35 should be provided so that at least adjacent water-absorbent resin presence regions 3c, 3c are independent of one another. The reason is as follows. The water-absorbent resin 33 has a property of swelling and spreading into the space. Due to this, if no sealing portions are present in the sheet-like absorbent layer even with the water-absorbent resin absence regions formed therein, then the swelling water-absorbent resin are spread over entire surfaces between the nonwoven fabric sheets that constitute the sheet-like water-absorbent layer, and it is impossible to secure gaps between the sheet-like water-absorbent layer and the fiber assembly layer. Besides, the swelling water-absorbent resin prevents permeation of the body fluid excreted the second time and the following. It is noted that the water-absorbent resin powder may be present in the water-absorbent resin powder absence regions that constitute the respective sealing portions 35 as long as the powder does not influence the sealing portions.

The sealing portions need to have strength sufficient to prevent breakage by the swelling of the resin. As means for forming such sealing portions, the same means as that for the fiber assembly layer can be adopted. Similarly to the gap portions of the fiber assembly layer, the sealing portions provided on the sheet-like water-absorbent layer can be provided either linearly or intermittently along the water-absorbent resin absence regions. Unsealed parts of the sheet-like water-absorbent layer that is intermittently sealed function as expansion margins when the water-absorbent resin powder swells. In addition, the shape of the sealing portions is not limited to the linear shape and may be zigzag or the other shape (see FIG. 9A and FIG. 9B.

If resin powder absence regions other than the end regions 3a and the intermediate regions 3b are provided in parallel to the width direction of the sheet-like water-absorbent layer, the regions may be used as the sealing portions. This makes it easier to cut the sheet-like water-absorbent layer 3 in manufacturing steps.

The absorbent mat which the absorbent article according to the present invention includes is formed by superimposing the sheet-like water-absorbent layer 3 on the fiber assembly layer 2. To prevent the absorbent article from being twisted or deformed during use, the fiber assembly layer 2 may be fixedly bonded to the sheet-like water-absorbent layer 3 by means such as an adhesive. It is noted, however, that the adhesive layer is preferably formed to be netted so as to prevent the generation of the cavities 5 after the water absorption and to secure the air-permeability and the like of the absorbent article. As the adhesive used herein, the same adhesive as that used for the sheet-like water-absorbent layer 3 can be used.

To secure the sufficient amount of absorption, the absorbent mat may have a multilayer structure of two or more sheet-like water-absorbent layers 3 and/or fiber assembly layers 2. If the multilayer structure of two or more sheet-like water-absorbent layers 3 is to be provided, a plurality of sheet-like water-absorbent layers 3 may be simply superimposed or a wide sheet-like water-absorbent layer 3 may be folded. If the multilayer structure is formed by folding a single wide sheet-like water-absorbent layer 3, the multilayer structure can be easily manufactured and the necessary amount of absorption can be secured as long as the single sheet-like water-absorbent layer 3 is folded at a center thereof in the width direction or edges of the layer 3 in the width direction are folded downward or upward.

To employ the sheet-like water-absorbent layers 3 having this multilayer structure, it is preferable that the water-absorbent resin powder presence regions 3c of the respective sheet-like water-absorbent layers 3 are superimposed so as to reduce a backflow amount of the absorbent article that uses the sheet-like water-absorbent layers 3, and to ensure high absorption speed and high diffusion ability. The water-absorbent resin powder presence regions 3c of the upper and lower sheet-like water-absorbent layers 3 are superimposed, whereby the thickness of each sheet-like water-absorbent layer 3 after swelling is increased and the distance between the fiber assembly layer and the skin of the wearer is further widened. The effect of suppressing the backflow phenomenon of the body fluid is therefore improved. If the water-absorbent resin powder presence regions 3c are superimposed on the sealing portions 35, the cavities 5 is not effectively formed and the body fluid excreted the second time and the following is not smoothly absorbed. To keep this multilayer structure stable, the sheet-like water-absorbent layers are preferably bonded and fixed to one another.

Figure 11:
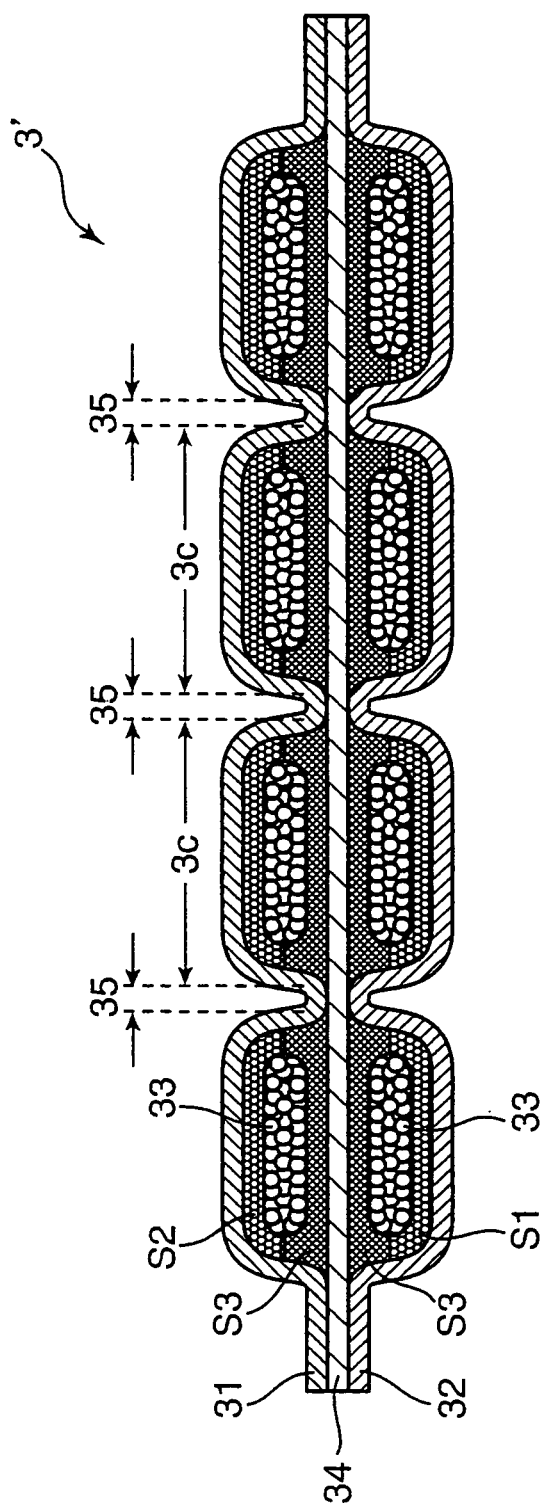
FIG. 11 is a schematic cross-sectional view that illustrates a multilayer structure of the sheet-like water-absorbent layer.

As illustrated in FIG. 11, a sheet-like water-absorbent layer 3' configured so that adhesive layers S1, S2 and S3 are provided among three nonwoven fabric sheets, i.e., between the first nonwoven fabric sheet 32 and an intermediate nonwoven fabric sheet 34, and between the intermediate nonwoven fabric sheet 34 and the second nonwoven fabric sheet 32, respectively, and so that the water-absorbent resin layers 3 adhere to the adhesive layers S1, S2 and S3 can be employed. Manners of applying the respective adhesive layers S1, S2 and S3 can be arbitrarily selected, and each of the adhesive layers S1, S2 and S3 may be netted so that many filamentous adhesives randomly adhere to one another or spiral.

In this sheet-like water-absorbent layer 3', only one nonwoven fabric sheet is present between the upper and lower layers of the water-absorbent resin powder 33 in the thickness direction. Consequently, as compared with the sheet-like water-absorbent layer formed by folding the sheet-like absorbent layer 3 or superimposing a plurality of sheet-like absorbent layers 3, manufacturing steps can be simplified and a cost of the absorbent article itself can be reduced. In addition, as compared with the sheet-like water-absorbent layer formed by folding the sheet-like water-absorbent layer 3, it suffices to manufacture a narrow sheet and a folding step is unnecessary. A manufacturing space can be therefore eliminated.

Figure 12:
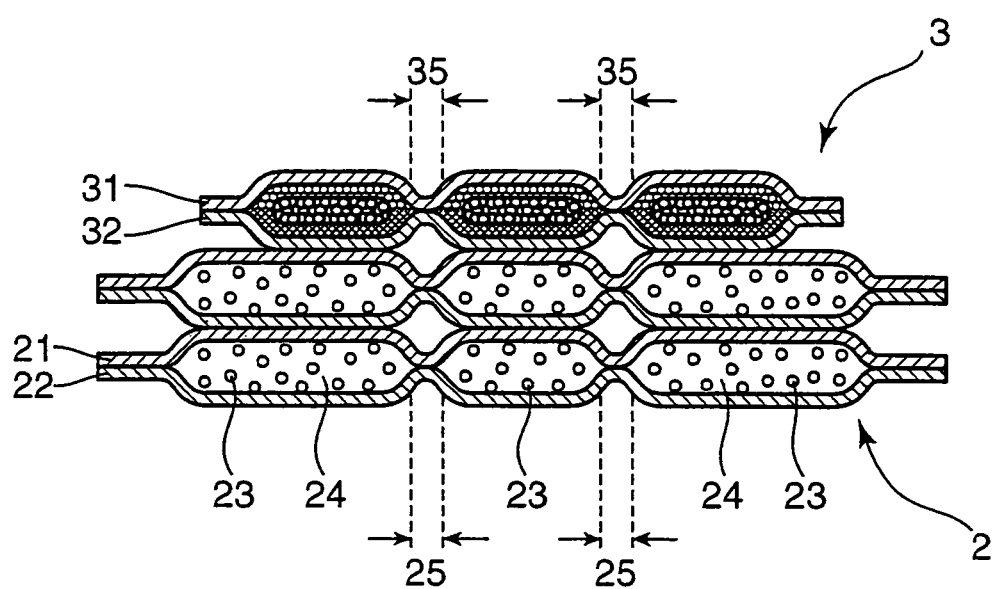
FIG. 12 is a schematic cross-sectional view that illustrates another multilayer structure of the sheet-like water-absorbent layer.

To employ the fiber assembly layers 2 having the multilayer structure, it is preferable that all of or a part of the gap portions 25 of the upper and lower fiber assembly layers 2 are superimposed so as to accelerate diffusion of the body fluid (FIG. 12). If too many fiber assembly layers 2 are used, the thickness of the absorbent mat is increased. As a result, the wearer feels stiff in the hip joint and feels quite uncomfortable. The number of the fiber assembly layer 2 may be, therefore, appropriately determined.

If either the gap portions 25 of the fiber assembly layer 2 or the sealing portions 35 of the sheet-like water-absorbent layer 3 are formed zigzag, for example., the gap portions are formed linearly and the sealing portions are formed zigzag, it is preferable that the lower gap portions 25 and the upper sealing portions 35 are superimposed in most parts.

Furthermore, a diffusion sheet equal in area to the absorbent mat may be arranged below the fiber assembly layer 2 of the absorbent mat. By providing the diffusion sheet, drained water can be diffused over entire regions of the absorbent article in the longitudinal direction. A material for the diffusion sheet is preferably a liquid-permeable nonwoven fabric such as an air-through nonwoven fabric, a point-bonded nonwoven fabric or a spunlace nonwoven fabric obtained by treating hydrophobic fiber such as polypropylene (PP), polyethylene (PE) or polyethylene terephthalate (PET) fiber by a surfactant. More preferably, the diffusion sheet contains hydrophilic fiber such as rayon fiber or cotton fiber.

A preferred embodiment of a method for manufacturing the absorbent mat included in the absorbent article according to the present invention will next be described. First, a continuous sheet-like water-absorbent layer having the sheet-like absorbent layer formed continuously in the longitudinal direction is manufactured on a dedicated sheet-like water-absorbent layer manufacturing line, cut to have a predetermined width, and wound into a roll. On a different manufacturing line (which is preferably an absorbent article manufacturing line) from the sheet-like water-absorbent layer manufacturing line, a continuous body of the fiber assembly layer (a continuous fiber assembly layer) corresponding to the lower layer of the absorbent mat is manufactured. While drawing out the continuous sheet-like water-absorbent layer from the roll and causing the fiber assembly layer to run on the sheet-like water-absorbent layer, the hot melt adhesive is applied onto a bonded surface on which the fiber assembly layer is bonded to the sheet-like water-absorbent layer. While causing the continuous fiber assembly layer to run, the sheet-like water-absorbent layer is mounted on the fiber assembly layer, and bonded to and integrated with the fiber assembly layer. The continuous absorbent mat thus obtained is pressurized to stabilize the shape of the mat, and cut to pieces each by a desired size, thereby obtaining individual absorbent mats. The absorbent mats thus obtained are arranged between the liquid-permeable top sheet and the liquid-impermeable back sheet by the conventionally well-known method, thereby providing an absorbent article or an absorbent for an absorbent article. If the sheet-like water-absorbent layer is smaller in area than the fiber assembly layer, then the hot melt adhesive may be applied to the sheet-like water-absorbent layer cut to have a predetermined length in advance, and the resultant sheet-like absorbent layer may be transferred onto an appropriate portion on the fiber assembly layer (e.g., a central region of the absorbent article corresponding to the hip join) to provide the absorbent mat. The process may be then introduced into the absorbent article manufacturing line.

Moreover, if the fiber assembly layers of the respective absorbent articles are manufactured on the line intermittently with the use of a pattern drum or the like, then the sheet-like water-absorbent layer cut to have the predetermined length in advance is integrated with the fiber assembly layer to thereby provide the absorbent mat, and the process is introduced into the absorbent article manufacturing line so as to manufacture the absorbent article similarly to the above method.

The absorbent mat obtained as described above is held between the liquid-permeable top sheet and the liquid-impermeable back sheet so that the sheet-like water-absorbent layer is located on the top sheet (wearer) side. The resultant absorbent article can be used as a disposable diaper or a urine absorbing pad. Alternatively, the absorbent mat may be held between the top sheet and the back sheet, and can be used as an absorbent for disposable pants. To manufacture a disposable absorbent article such as the disposable diaper, the urine absorbing pad or the disposable pants, a well-known shape and a well-known structure thereof can be adopted and various well-known members used for the disposable absorbent article can be attached thereto.

Figure 13:
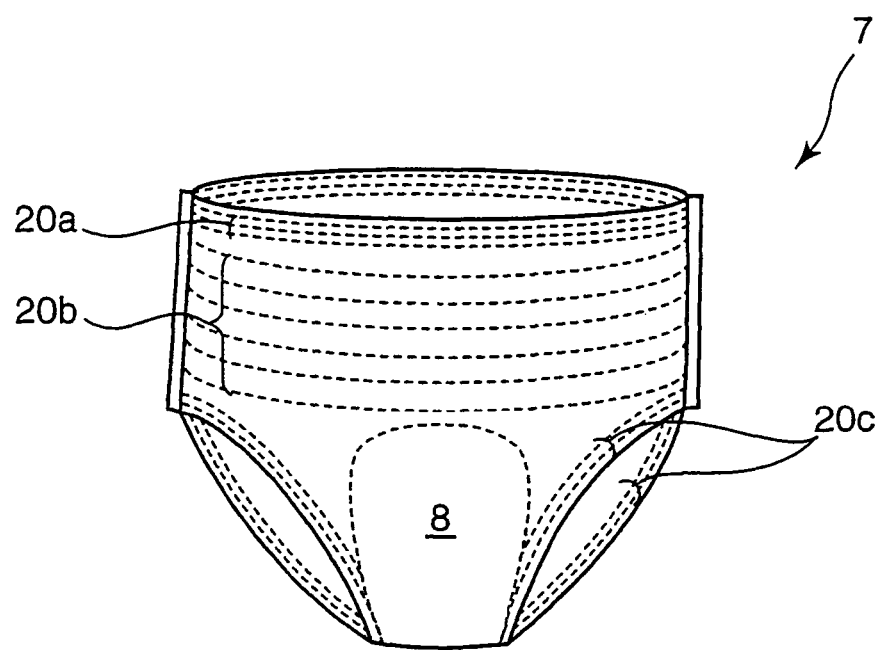
FIG. 13 illustrates a specific example of suitable disposable pants according to the present invention.
Figure 14:
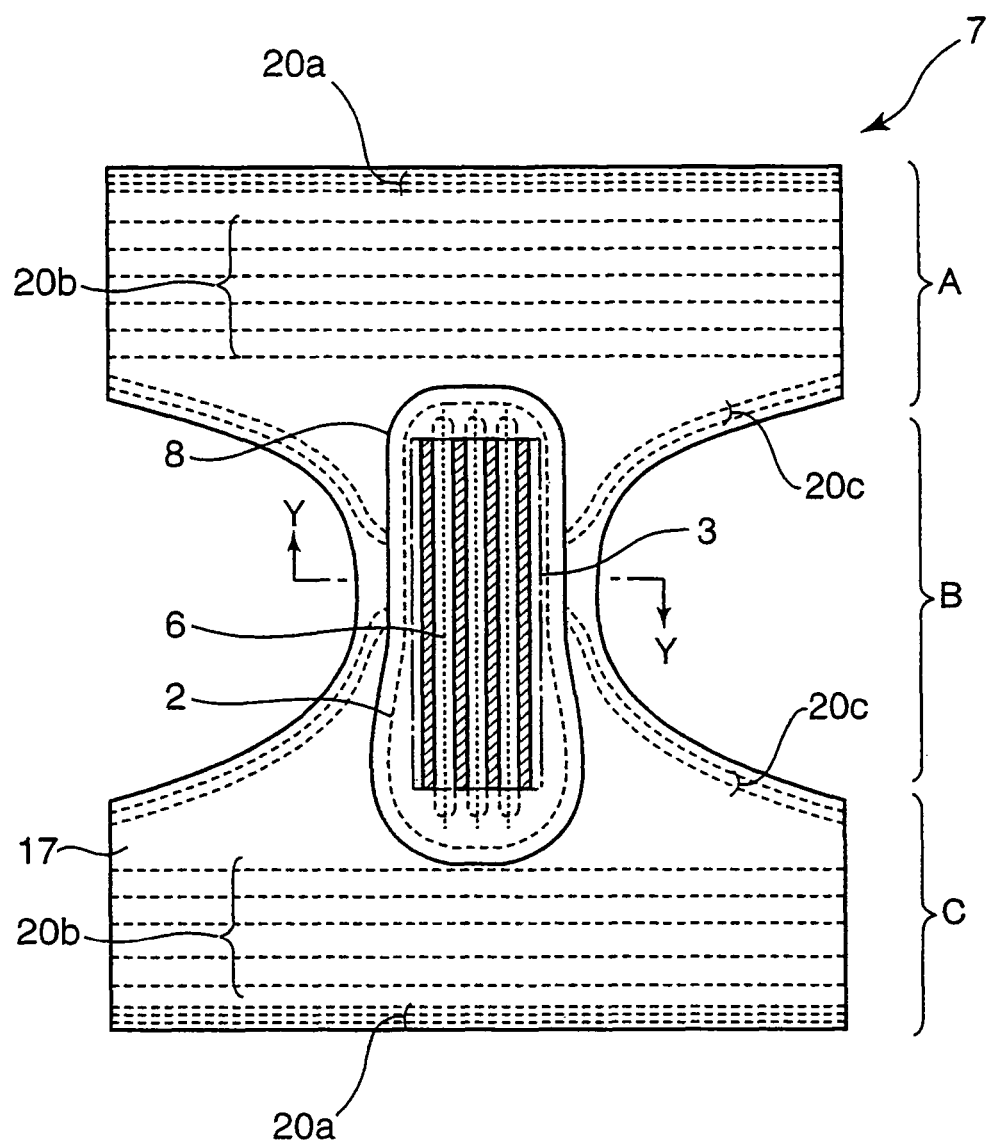
FIG. 14 is a plan view that illustrates a developed state of the disposable pants.
Figure 15A:
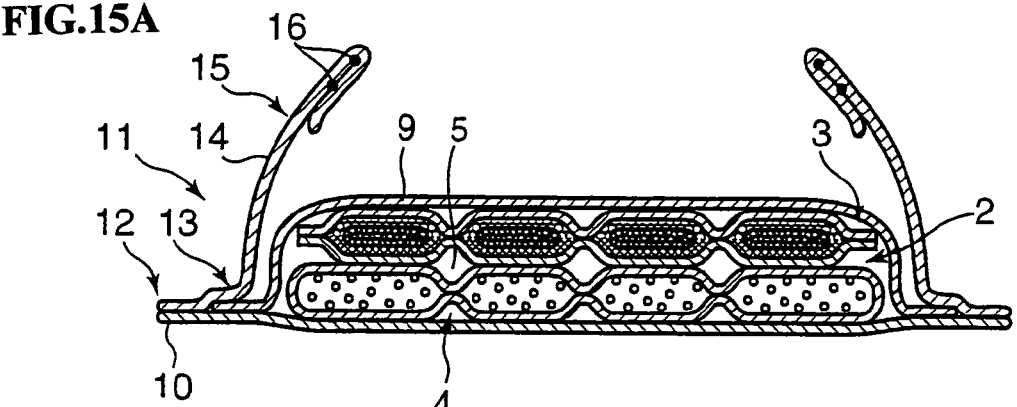
FIG. 15A, FIG. 15B, FIG. 15C, and FIG. 15D are schematic cross-sectional views of the disposable pants taken along a line Y-Y.
Figure 15B:
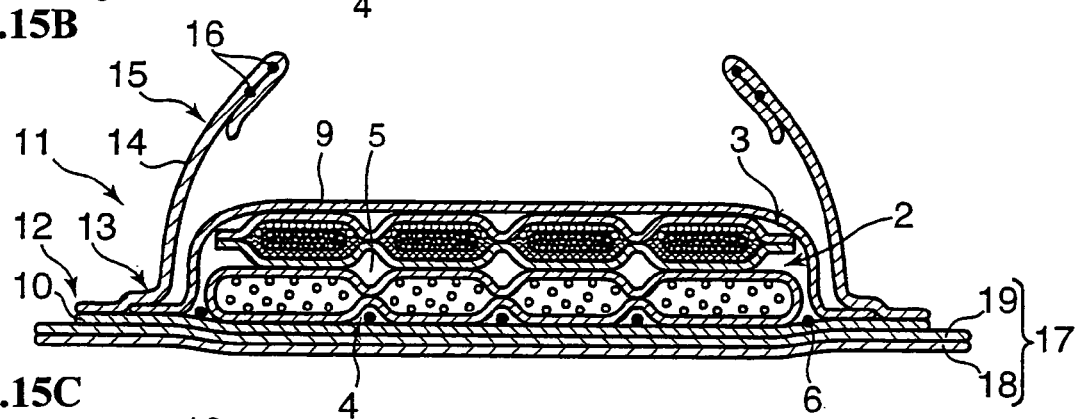
Figure 15C:
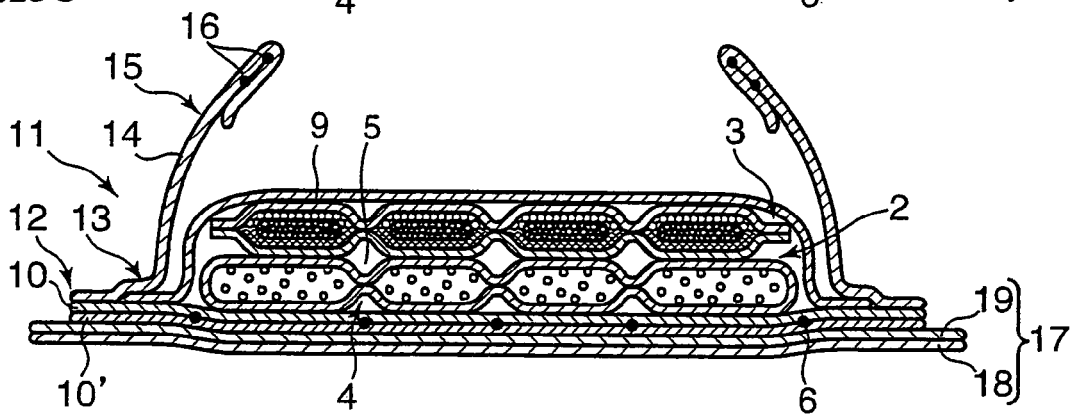
Figure 15D:
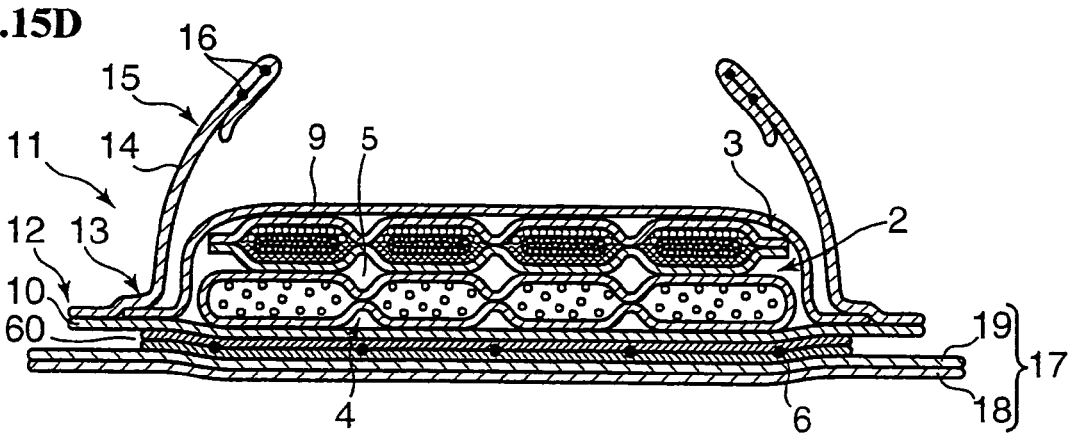

FIG. 13, FIG. 14 and FIG. 15A to FIG. 15D illustrate disposable pants as a preferred embodiment of the absorbent article according to the present invention. FIG. 13 is a front view of disposable pants 7, FIG. 14 is a plan view that illustrates a developed state of the disposable pants illustrated in FIG. 13, and FIG. 15A is sectional view taken along a ling Y-Y of FIG. 14, showing only an absorbent 8 illustrated in FIG. 14. As the absorbent for these disposable pants 7, the absorbent mat described so far is employed. This absorbent 8 is configured as follows. The absorbent mat 1 is held between the liquid-permeable top sheet 9 and the liquid-impermeable back sheet 10 so that the sheet-like water-absorbent layer 3 is located on the top sheet 9 (wearer) side. A liquid-impermeable side sheet 11 is then provided to cover bottoms and side portions of the absorbent mat 1.

The side sheet 11 is bonded to the top sheet 9 and the back sheet 10 in flap portions 12 provided in outer extensions on the bottoms of the absorbent mat 1, respectively. On the absorbent mat 1 side of each flap portion 12, the top sheet 9 is bonded to the back sheet 10 so as to hold the top sheet 9 between the back sheet 10 and the side sheet 11 (to provide a rising end 13). Further, the side sheet 11 includes a rising portion 14 rising upward from the rising end 13. The side sheet 11 is substantially equal in length to the absorbent 8, faced down on front and rear ends of the absorbent 8, and bonded to an upper surface of the top sheet 9 (not illustrated).

A tip end of the rising portion 14 is folded inward of the width direction of the absorbent mat 1 (to form a solid seal portion 15), an elastic member 16 for the solid is provided within the solid seal portion 15 in an expanded state, and the folded side sheets 11 are bonded together in the solid seal portion 15. In such rising portion 14, the inner edge 16 rises to follow the skin of the wearer with the rising end 15 used as a proximal end to prevent the lateral leakage of the body fluid to the hip joint when the wearer wears the absorbent article 10.

This absorbent 8 is arranged in a lower portion of a central hip joint part of a multilayer sheet 7 that provides the shape of pants, and both sides of the multilayer sheet 17 are bonded together by the heat seal or the like, thereby forming the disposable pants 7. The multilayer sheet 17 consists of an outermost layer sheet 18 and an inner layer sheet 19 arranged just inside of the layer 18. With a view of improving the wear's sense of fit to the pants 7 when the wearer wears the pants 7 and preventing leakage of urine from the gaps generated between the wearer and the absorbent article, a waist elastic member 20a is added to a waist opening, a plurality of body-fit elastic members 20b are added to a front or belly region A and a back region C to be interposed between the outermost layer sheet 18 and the inner layer sheet 19 in expanded states, respectively, and a plurality of leg elastic members 20c are added along edges of the leg openings in expanded states, respectively.

The locations of the elastic members 6 are not limited to those in the fiber assembly layer 2. The elastic members 6 may be provided in the fiber assembly layer 2 on the back sheet 10 as illustrated in FIG. 15B. Alternatively, another sheet 10' may be arranged outside the back sheet 10 to provide a two-layer structure, and the elastic members 6 may be held between these sheets 10 and 10' (FIG. 15C). Additional sheets 60 between which the elastic members 6 are held may be provided between the back sheet 10 and the multilayer sheet 17 (FIG. 15D). In any case, it is preferable that the elastic members 6 are provided at positions corresponding to the respective fiber absence regions 2b of the fiber assembly layer 2.

Since it is necessary to speedily capture the body fluid (excretion) from the wearer and move the body fluid to the absorbent mat 1, a liquid-permeable sheet material is preferably used for the liquid-permeable top sheet 9. Specifically, examples of the liquid-permeable sheet material include liquid-permeable sheet materials normally used for disposable absorbent articles such as a nonwoven fabric using hydrophilic fibers such as cellulose, rayon or cotton fibers, a nonwoven fabric using hydrophobic fibers such as polypropylene, polyethylene, polyester or polyamide fibers, a surface of each of which is treated by the surfactant, and a plastic film including openings.

A water-repellant or liquid-impermeable sheet material is preferably used for the liquid-impermeable back sheet 10 so as to prevent the body fluid absorbed by the absorbent mat 1 from oozing outside the absorbent article 10. More preferably, examples of the material include water-repellant nonwoven fabrics normally used for disposable diapers (e.g., spun-bonded nonwoven fabrics, meltblown nonwoven fabrics, and SMS nonwoven fabrics), a plastic film (preferably air-permeable plastic film), and composite materials thereof.

The same material as that for the back sheet 10 is used for the side sheet 11.

The flap portions 14 for bonding the top sheet 9, the back sheet 10, and the side sheet 11, and the solid seal portions 15 for bonding the side sheets 11 may bond the targets by the bonding method such as heat seal bonding, hot melt adhesive bonding, or ultrasonic bonding.

As the elastic members 16 for the solid provided inward of the tip ends of the rising portions 14 and the elastic members 20a to 20c, elastic members normally used for disposable diapers and consisting of, for example, polyurethane or natural rubber may be used. Such a material can be used in a filamentous or film form. These elastic members are fixed to the respective additional regions in expanded states by the bonding method such as thermal fusion bonding, hot melt adhesive bonding, or ultrasonic bonding.

Although FIG. 13, FIG. 14 and FIG. 15A to FIG. 15D illustrate the pants type absorbent article by way of example, the present invention is not limited thereto. Various absorbent articles such as the disposable diaper, the urine absorbing pad, and tape-added disposable diaper fall within the technical scope of the present invention.

This application is based on Japanese Patent Application No. 2003-131741 filed with Japan Patent Office on May 9, 2003, the contents of which are hereby incorporated by reference.

Although the present invention has been fully described by way of example with accompanying drawings, it is to be understood that various changes and modifications will be apparent to those skilled in the art. Therefore, unless otherwise such changes and modifications depart from the scope of the present invention hereinafter defined, they should be construed as being included therein.

Industrial Applicability

By adopting the aforementioned structure, the present invention provide the absorbent article having improved absorption speed, improved diffusion property, improved absorption amount, and having the backflow property suppressed to lower level.

The invention claimed is:

1. A disposable absorbent article, comprising:
  a liquid-permeable top sheet;
  a liquid-impermeable back sheet; and
  an absorbent mat provided between said liquid-permeable top sheet and said liquid-impermeable back sheet, the absorbent mat including a water-absorbent layer in a general form of a sheet that contains a water-absorbent resin powder but that does not contain pulp fibers, and a fiber assembly layer that contains both the water absorbent resin powder and the pulp fibers, the water-absorbent layer and the fiber assembly layer being arranged sequentially in this order from a top sheet side,
  the water-absorbent layer including a first nonwoven fabric sheet and a second nonwoven fabric sheet,
  the water-absorbent layer further including water-absorbent resin powder presence regions in which the water-absorbent resin powder is present, and water absorbent resin powder absence regions which is formed between the water-absorbent resin powder presence regions, the water-absorbent resin powder presence regions and the water-absorbent resin powder absence regions being formed to be adjacent with one another between said first nonwoven fabric sheet and said second nonwoven fabric sheet,
  the first nonwoven fabric sheet and the second nonwoven fabric sheet of the water-absorbent layer being bonded to each other in the water-absorbent resin powder absence regions,
  the fiber assembly layer including a fiber presence region in which both the pulp fibers and the water-absorbent resin powder are present, and a fiber absence region, which is formed between the fiber presence regions, in which both the pulp fibers and the water-absorbent resin powder are absent, the fiber presence region and the fiber absence region being formed to the adjacent with each other, said fiber assembly layer further including an upper nonwoven fabric sheet and a lower nonwoven fabric sheet, the fiber presence region and the fiber absence region being formed between the upper nonwoven fabric sheet and the lower nonwoven fabric sheet, each said fiber presence region being wrapped up with the upper nonwoven sheet and the lower nonwoven sheet, the upper nonwoven fabric sheet and the lower nonwoven fabric sheet being bonded together at the fiber absence region so as to form a cavity between said liquid-impermeable back sheet and said fiber assembly layer, a surface of said liquid-impermeable back sheet comprising a part of a boundary which defines said cavity,
  wherein the water absorbent layer and of the fiber assembly layer are detached at each location of the water-absorbent resin powder absence region and the fiber absence region.

2. The disposable absorbent article according to claim 1, wherein the water-absorbent layer is superimposed on the fiber assembly layer so that all of or a part of the water-absorbent resin powder absence regions of said water-absorbent layer are located on the fiber absence region of said fiber assembly layer.

3. The disposable absorbent article according to claim 1, wherein the first nonwoven fabric sheet and the second nonwoven fabric sheet of the water-absorbent layer are thermally bonded to each other in the water-absorbent resin powder absence regions.

4. A disposable absorbent article, comprising:
  a liquid-permeable top sheet;
  a liquid-impermeable back sheet; and
  an absorbent mat provided between said liquid-permeable top sheet and said liquid-impermeable hack sheet, the absorbent mat including a water-absorbent layer in a general form of a sheet that contains a water-absorbent resin powder but that does not contain pulp fibers and a fiber assembly layer that contains both the water absorbent resin powder and the pulp fibers, the water-absorbent layer and the fiber assembly layer being arrange sequentially in this order from a top sheet side, the fiber assembly layer including a fiber presence region in which both the pulp fibers and the water-absorbent resin powder are present, and a fiber absence region in which both the pulp fibers and the water-absorbent resin powder are absent, the fiber presence region and the fiber absence region being formed to the adjacent with each other said fiber assembly layer further including an upper nonwoven fabric sheet and a lower nonwoven fabric sheet the fiber presence region and the fiber absence region being formed between the upper nonwoven fabric sheet and the lower nonwoven fabric sheet each said fiber presence region being wrapped up with the upper nonwoven sheet and the lower nonwoven sheet, the upper nonwoven fabric sheet and the lower nonwoven fabric sheet being bonded together at the fiber absence region so as to form a cavity between said liquid-impermeable back sheet and said fiber assembly layer a surface of said liquid-impermeable back sheet comprising apart of a boundary which defines said cavity, the fiber absence region of the fiber assembly layer being formed in a longitudinal direction of the absorbent article, and an elastic member being bonded to the fiber absence region of the fiber assembly layer in an expanded state along the longitudinal direction.

5. The disposable absorbent article according to claim 1, wherein the fiber absence region of the fiber assembly layer is formed in a longitudinal direction of the absorbent article, and an elastic member is bonded to the back sheet on a fiber absence region side of the fiber assembly layer or to the back sheet through another sheet in an expanded state along the longitudinal direction.

* * * * *